US008420070B2

(12) United States Patent
Simchoni-Barak et al.

(10) Patent No.: US 8,420,070 B2
(45) Date of Patent: Apr. 16, 2013

(54) CONTROLLING SUGAR FEEDING INSECTS

(75) Inventors: Miri Simchoni-Barak, Kibutz Iftach (IL); Yosef Schlein, Jerusalem (IL); Gunter C. Muller, Freising (DE)

(73) Assignee: Westham Ltd., Tel Aviv (IL)

( * ) Notice: Subject to any disclaimer, the term of this patent is extended or adjusted under 35 U.S.C. 154(b) by 114 days.

(21) Appl. No.: 11/692,955

(22) Filed: Mar. 29, 2007

(65) Prior Publication Data

US 2007/0269404 A1 Nov. 22, 2007

Related U.S. Application Data

(60) Provisional application No. 60/747,820, filed on May 22, 2006.

(51) Int. Cl.
*A01N 25/00* (2006.01)
(52) U.S. Cl.
USPC .......................................................... 424/84
(58) Field of Classification Search .................. None
See application file for complete search history.

(56) References Cited

U.S. PATENT DOCUMENTS

| | | | | |
|---|---|---|---|---|
| 4,983,390 | A * | 1/1991 | Levy | 424/404 |
| 5,683,687 | A * | 11/1997 | Marin et al. | 424/84 |
| 6,593,299 | B1 * | 7/2003 | Bennett et al. | 424/408 |
| 6,821,526 | B1 | 11/2004 | Huang | |
| 2002/0146394 | A1 * | 10/2002 | Stamets | 424/93.5 |
| 2004/0057976 | A1 * | 3/2004 | Warner et al. | 424/410 |

FOREIGN PATENT DOCUMENTS

| | | |
|---|---|---|
| EP | 1477061 | 3/2005 |
| JP | 2004315508 A * | 11/2004 |
| WO | WO2004/012505 | 2/2004 |
| WO | WO2004/093538 | 4/2004 |

OTHER PUBLICATIONS

Wolfe et al., Israel Journal of Plant Sciences (1995), vol. 43, No. 4, pp. 325-337 (Abstract). BIOSIS[online]. Retrieved from :STN.*
Muller et al., Journal of Vector Ecology (2004), vol. 29, No. 1, pp. 154-158 (Abstract). BIOSIS [online]. Retrieved from: STN.*
Ali et al. Tamarix nilotica-a flood tolerant desert plant. 13. Jahrestagnung der Deustschen Gesellschaft fur Tropenokologie 1.-3. Mar. 2000 in Wuzburg (2000)[online], [retrieved on Aug. 22, 2008]. Retrieved from the Internet<URL://www.desertconsult.de/PDF/22_Tamarix_GFOE.pdfl>.*
Rousseu, ed., Handbook of Separation Process Technology (1987), pp. 129, 167, 169, 172-175, 540, 551, 552.*
Di Luca et al. Parassitologia (2006), vol. 48, No. 1-2, p. 155 (Abstract). BIOENG[online]. Retrieved from :STN.*
Xue et al., Boric Acid Bait Kills Adult Mosquitoes (Diptera: Culicidae), J. Econ. Entomology (2003), vol. 96, No. 5, pp. 1559-1562.*
Beavers, G.M., Hanafi, H.A., & Dykstra, E.A., 2004, Evaluation of 1-octen-3-ol and carbon dioxide as attractants for *Phlebotomus papatasi* (Diptera: Psyhodidae) in southern Egypt J. Am. Mosq. Contr. Assoc. 20: 130-133, Journal.
Kline, D.L., 2007. Semiochemicals, traps/targets and mass trapping technology for mosquito management. American Mosquito Control Association (AMCA), Bulletin. 23(7, supplement to No. 2): 241-251, Journal.
Bernier,U.R., Booth, M.M., & Yost, R.A., 1999. Analysis of human skin emanations by gas chromatography/mass spectrometry. 1. Thermal desorption of attractants for the yellow fever mosquito (*Aedes aegypti*) from handled glass beads. Anal. Chem. 1999, 71: 1-7, Journal.
Kline, D.L. Takken, W., Wood, J.R., & Carlson, D.A., 1990. Field studies of the potential of butanone, carbone dioxide, honey extract, 1-octen-3-ol, L-lactic acid and phenols as attractants for mosquitoes. Med. Vet. Entomol. 4: 383-391, Journal.
Orshan, L., Szekely, D., Khalfa, Z., & Bitton, S., 2010. Distribution and seasonality of Phlebotomus sand flies in cutaneous leishmaniasis foci, Judean Desert, Israel. J. Med. Entomol. In Press, Journal.
Vale, G.A., 1985. The use of I-octen-3-ol, acetone and carbon dioxide to improve baits for tsetse flies, *Glossina* spp. (Diptera: Glossinidae). Bull. Ent. Res. 75: 219-231, Journal.
Vythilingam I., Lian, C.G., & Thim, C.S., 1992. Evaluation of carbon dioxide and 1-octen-3ol as mosquito attractants. Southeast Asian J. Trop. Med. Public Health. 23: 328-331, Journal.
Bradbury, W.C. & Bennett, G.F., 1974. Behavior of adult simuliidae (diptera). II. vision and olfaction in near-orientation and landing. Can. J. Zool. 52: 1355-1364, Journal.
Prokopy, R.J. & Owens, E.D., 1978. Visual generalist with visual specialist phytophagous insects: host selection behaviour and application to management. Ned. Entomol. Vet. Amsterdam Proceedings 4th Insect/Host Plant Symposium. Ent. exp. & appl. 24: 409-420, Journal.
Silberglied, R.E., 1979. Communication in the ultraviolet. Ann. Rev. Ecol Syst. 10: 373-98, Journal.
Prokopy, R.J. & Owens, E.D., 1983. Visual detection of plants by herbivorous insects. Ann. Rev. Entomol. 28: 337-64, Journal.
Allan, S.A., Day, J.F., & Edman, J.D., 1987. Visual ecology of biting flies. Ann. Rev. Entomol. 32: 297-316, Journal.
Kusakabe, Y. & Ikeshoji, T., 1990. Comparative attractancy of physical and chemical stimuli to aedine mosquitoes. Jpn. J. Sanit. Zool. 41(3): 219-225, Journal.
Sutcliffe, J.F., Steer D.J., & Beardsall, D., 1995. Studies of host location behaviour in the black fly simulium arcticum (IIS-10.11) (diptera: simuliidae): aspects of close range trap orientation. Bulletin of Entomological Research. 85: 415-424, Journal.
Gibson, G. & Torr, S.J., 1999. Visual and olfactory responses of haematophagous diptera to host stimuli. Med. Vet. Entomol. 13: 2-23, Journal.

(Continued)

*Primary Examiner* — James H Alstrum Acevedo
*Assistant Examiner* — Frank Choi
(74) *Attorney, Agent, or Firm* — Reuven K. Mouallem

(57) ABSTRACT

Methods for controlling sugar feeding insects by a chemical compositions which includes mixing an extract of flowers and of fruit, or their components in water with predetermined amount of sugar mixture and oral toxin. The methods also concern applying an effective amount of the insect bait to an area to be controlled and trapping or killing the insects by a bait stations. Methods of applying and the parameters of choosing a suitable location for applying the bait are disclosed.

24 Claims, 5 Drawing Sheets

OTHER PUBLICATIONS

Mann, R.S., Kaufman, P.E., & Butler, J.F., 2009. *Lutzomyia* spp. (diptera: psychodidae) response to olfactory attractant- and light emitting diode-modified Mosquito Magnet X (MM-X) traps. J. Med. Entomol. 46(5): 1052-1061, Journal.

W.M. Wheeler, Ants: Their Structure, Development and Behavior, Columbia University Press, New York, 1910, 663 pages, Book.

J.C. Trager, Advances in Myrmecology, E.J. Brill/W.S. Heinman Co., Inc., New York, 1988, 551 pages, Book.

R.K. Vander Meer, K. Jaffe, and A. Cedeno, Applied Myrmecology: A World Perspective, Westview Press, Boulder, 1990, 741 pages, Book.

B. Holldobler and E. O. Wilson, The Ants, Belknap Press of Harvard University Press, Boston, 1990, 746 pages, Book.

C.R. Huxley and D.F. Cutler, Ant-Plant Interactions, Oxford University Press, New York, 1991, 601 pages, Book.

D.F. Williams, Exotic Ants: Biology, Impact, and Control of Introduced Species, Westview Press, Boulder, 2000, 332 pages, Book.

Vargo, A.M. & Foster, W.A., 1982. Responsiveness of Female *Aedes aegypti* (Diptera: Culicidae) to Flower Extracts. J. Med. Entomol. 19(6):710-718.

De Meillon, B., Sebastian, A., & Khan, Z.H., 1967. Cane-sugar feeding in Culex pipiens fatigans. Bull. WHO 36: 53-65.

Jepson, P.C. & Healy, T.P., 1988. The location of floral nectar sources by mosquitoes: an advanced bioassay for volatile plant odours and initial studies with *Aedes aegypti* (L.) (Diptera: Culicidae). Bull. Entomol. Res. 78:641-650.

Foster, W. A. & Hancock, R.G., 1994. Nectar related olfactory and visual attractants for mosquitoes. J. Am. Mosq. Control Ass. 10: 288-296.

Mauer, D.J. & Rowley, W.A., 1999. Attraction of Culex pipiens pipiens (Diptera: Culicidae) to flower volatiles. J. Med. Entomol. 36(4):503-507.

Takken, W. & Knols, B.G.J., 1999. Odor-mediated Behavior of Afrotropical Malaria Mosquitoes. Annu. Rev. Entomol. 44:131-157.

Foster, W.A. & Takken, W., 2004. Nectar-related vs. blood related volatiles: behavioural response and choice by female and male *Anopheles gambiae* (Diptera: Culicidae) between emergence and first feeding. Bull. Entomol. Res. 94:145-157.

Yuval, B., 1992. The Other Habit: Sugar Feeding by Mosquitoes. Bull. Soc. Vector Ecol., 17(2): 150-156.

Roitberg, B.D., and Friend, W.G., 1992. A General Theory for Host Seeking Decisions in Mosquitoes. Bull. Math. Biol., 54(2/3): 401-412.

Foster, W.A., 1995. Mosquito Sugar Feeding and Reproductive Energetics. Annu. Rev. Entomol., 40:443-74.

Hancock, R.G., and Foster, W.A., 1997. Larval and adult nutrition effects on blood/nectar choice of *Culex nigripalpus* mosquitoes. Medical and Veterinary Entomology, 11:112-122.

Sarkar, E., 2010. Sweet bait kills malaria mosquitoes. Times Wellness, Source: http://www.timeswellness.com/index.aspx? p.=article§id=11&contentid=2010111220101111117272780372d65c32.

McNeil, D.G., Jr., 2011. Brewing Up Double-Edged Delicacies for Mosquitoes. The New York Times, Sep. 27, 2011: D2.

McNeil, D.G., Jr., 2011. Poisoned nectar is a double-edged delicacy for mosquitoes. The Indian Express, Source: http://www.indianexpress.com/news/poisoned-nectar-is-a-doubleedged-delicacy-formosquitoes/854406/.

Black, H., 2012. Sweet Rewards. American Way, 45(6): 40-43.

Ed. Chin, G. and Yeston, J., 2006. Editor's Choice: The Sweet Taste of Death. Science, 313: 592.

Ed., 2010. New Method for Control of Malaria Applied in Africa. Science Daily, Source: http://www.sciencedaily.com/releases/2010/11/101108102604.htm.

Collins, L.E. & Blackwell, A., 2000. Colour cues for oviposition behavior in *Toxorhynchites moxtezuma* and *Toxorhynchites amboinensis* mosquitoes. J. Vector Ecology 25: 127-135.

Quarles, W., 2003. Mosquito attractants and traps. Common Sense Pest Control 19: 4-13.

Kawada, H., Takemura, S., Arikawa. K., & Takagi, M., 2005. Comparative study on nocturnal behavior of *Aedes aegypti* and *Aedes albopictus*. J. Med. Entomol. 42: 312-318.

Day, J.F., 2005. Host-seeking strategies of mosquito disease vectors. J. Amer. Mosq. Control Assoc. 21 (SP1) 17-22.

Williams, C.R., Bergbauer, R., Geier, M., Kline, D.L., Bernier, U.R., Russell, R.C. & Ritchie, S.A., 2006. Laboratory and field assessment of some kairomone blends for host-seeking *Aedes aegypti*. J. Amer. Mosq. Control Assoc. 22: 641-647.

Ball, T.S. & Ritchie, S.R., 2010. Evaluation of BG-Sentinel trap trapping efficacy for *Aedes aegypti* (Diptera: Culicidae) in a visually competitive environment. J. Med. Entomol. 47: 657-663.

Mexican Official Action in parallel prosecution of patent application No. 2008-014897, dated May 6, 2011 (Spanish).

Reporting letter for the above Mexican Official Action in parallel prosecution of patent application No. 2008-014897, by Mexian associate Ana Cecilia Rodriguez Luna, Patent Agent, from Calderon y De La Sierra y Cia., S.C., dated Jun. 15, 2011 (English).

Response to the above Mexican Official Action in parallel prosecution of patent application No. 2008-014897, dated Jul. 21, 2011 (Spanish).

Notice of Allowance for parallel Mexican patent application No. 2008-014897 by the Mexican Institute of Industrial Property, dated Nov. 10, 2011 (Spanish).

Translation of the above Notice of Allowance for parallel Mexican patent application No. 2008-014897, by the office of Mexican associate Calderon y De La Sierra y Cia. (English), (2011).

Gunter Muller, Yosef Schlein, Sugar questing mosquitoes in arid areas gather on scarce blossoms that can be used for control , International Journal for Parasitology 36(2006) 1077-1080.

B. Yuval , The Other Habit: Sugar Feeding by Mosquitoes. Bull.Soc. Vector Ecol. 17(2) Dec. 1992 pp. 1-7.

Woodbridge A. Foster, Mosquito Sugar Feeding and Reproductive Energetics, Dept. of Entomology , The Ohio State University , Columbus Ohio 43210,pp. 443-474, (1995).

* cited by examiner

CONTROLLING SUGAR FEEDING INSECTS

CROSS-REFERENCE TO RELATED APPLICATIONS

This application claims the benefit of U.S. Provisional Application Ser. No. 60/747,820 filed May 22, 2006, which is hereby incorporated by reference in its entirety.

FIELD OF THE INVENTION

The present invention relates to the field of entomology, and more particularly for attracting and exterminating mosquitoes and other blood sucking flying insects.

BACKGROUND OF THE INVENTION

Sugar is a vital part of the diet of male and female mosquitoes (Culicidae), sand flies (Phlebotomidae) and other sugar feeding insects, whether they are blood-sucking insects or whether they are non blood-sucking insects. Odors indicating sugars, emanate from rotting fruits, ripe fruits, sugar cane, honey, fermentation, scents of flowers and combination of the above. Sugar can also be found in nectar from flowers, from nectaries on leaves and stems, and honeydew excreted by homopterans [reviews by Yuval, B. 1992. The other habit: sugar feeding by mosquitoes. Bul. Soc. Vector Ecol. 17, 150-156. Foster, W. A. 1995. Mosquito sugar feeding and reproductive energetics. Ann. Rev. Entomol. 40, 443-474.]

A safe and fast acting method for controlling sugar-feeding insects, especially mosquitoes and sand flies is needed, in order to prevent transmission of diseases like malaria and eliminating bites and itching caused by such insects.

Current control methods include:
source reduction the removal of mosquito breeding habitats;
habitat modification
manipulating habitats to reduce breeding;
biocontrol: introducing natural predators of mosquitoes;
larvicide
using pesticides to reduce larval populations;
adulticide: using pesticides to reduce adult populations.

Source reduction can include overturning a tin can filled with water, or complex as permanently draining marshes.

Habitat modification, such as draining marshes or manipulating daily water flows can reduce mosquito populations but large-scale programs can be harmful to the ecosystem. Biological control is the use of natural enemies to manage mosquito populations. Effective biocontrol agents include predatory fish that feed on mosquito larvae such as *Gambusia affinis* and other small fish species.

Larval control can be achieved by dispersing dead spores of the natural soil bacteria *Bacillus thuringiensis*, especially Bt israelensis (BTI). BTI is used to interfere in the digestion systems of larvae. BTI can be dispersed by hand or dropped by helicopter in large areas.

Oils that increase the water tension of a water surface can be used as larvicides. Use of these oils causes the larvae and pupae to drown pupae because they cannot break the surface to obtain air. Such oils can be toxic or non-toxic.

Adulticide, using ground or aerial application of chemical pesticides, is less effective than the other methods of mosquito control and is generally considered a method of last resort. Ultra low volume (ULV) spraying of Malathion has been used in metropolitan areas like New York City to decrease the mosquito population and prevent the spread of West Nile Virus. Mosquitoes also have diseases that are caused by viruses, bacteria, fungi, protozoa, nematodes, and microsproidia but none of them is being used for control.

The most effective solutions for malaria control efforts in the third world are: mosquito nets, particularly nets treated with the insecticides permethrin or DDT. Nets are treated with insecticide because mosquitoes can sometimes get past an imperfect net.

Typically, a bait station device is employed to deliver an insecticide for the control of mosquitoes and other blood sucking flies. A number of bait stations and other devices of the like have been described in the art. For example, EP1477061 discloses an apparatus including an insect-collecting bag impregnated with an insecticide. The bag is connected to a suction inlet, suction action is effected by means of a motor-driven unit, A series of high luminosity LEDs and chemical action attracts the insects towards the entrance inlet subject to the suction action for their collection in the inner bag with insecticidal effect.

FR2851721 discloses a portable device for destruction of biting flying insects, which uses battery-powered electric motor with flexible cutter line attached to rotor.

WO2004093538 presents a long lasting insect baiting system containing wax (e.g., paraffin, GulfWax), a hardener (e.g., Elvax-60), an emulsifier (e.g., SPAN 60), an oil (e.g., food oils (preferably related to insect feeding) such as corn oil, molasses, glycerol or corn syrup), a chemical attractant (e.g., ammonium acetate or carbonate) and a phagostimulant (e.g., food such as proteinaceous materials such as protein and hydrolyzed protein or feeding stimulant, such as sugars like sucrose), optionally a visual attractant (e.g., food coloring), and optionally a toxicant (e.g., avermectin, methomyl, spinosad, phloxine B).

U.S. Pat. No. 6,821,526 discloses a device for controlling insects reservoir [of what? and absorbent material having a lower portion covered by non-absorbent material, and an upper portion with an insecticide.

WO2004012505 discloses methods for controlling insects using an insect bait useful to attract and control insects e.g. ants, flies, silverfish and cockroaches. The bait includes amino acids, a sugar and a preservative. The bait can be combined with an insect toxicant to effectively control and eliminate insect populations.

Studies by Muller & Schlein, 2006 [Müller G. and Schlein Y. 2006. Sugar questing mosquitoes in arid areas gather on scarce blossoms that can be used for control. *Int. J. Parasitol.* 36: 1077-1080], tested the whole population of *Anopheles sergentii* which was eliminated when lured by the fragrance of the flowers the mosquitoes fed on the poisonous sugar solution.

There is a need for a new approach for the control of sugar feeding insects, specifically mosquitoes and sand flies, by a different method of attraction.

The term "attractant" as used herein refers to an volatile chemical that causes in responsive organisms an olfactory signal to move along the increasing gradient towards the source of emanation. The "attractant" are blood-sucking flies in general, and in particular mosquitoes and sand flies.

SUMMARY OF THE INVENTION

According to the present invention there is provided an insecticidal composition for controlling sugar feeding insects including a feeding stimulant including sugar and an attractant of the insects which includes an extract, or extract active components, from flowers and/or fruit and an oral toxin toxic to the insects. The oral toxin is selected from the group including: spinosad between 0.05 and 0.5 volume percent in solvent or phloxin B between 0.3 and 3 volume percent in solvent or Boric Acid between 0.1 and 3 volume % in solvent. The solvent includes water and/or wine, or other hydrophilic volatile fluids such as ethanol methanol or acetone. The amount of sugar in the composition is between 5% and 80% by weight, the type of sugar used may be sucrose.

The attractant is selected from the group consisting of *Ochradenus* flower such as *Ochradenus baccatus* extract between 0.01 percent and 0.5 percent by volume or purified extract of fermenting fruit such as nectarine between 0.01 percent and 0.5 percent by volume or crude extract of fermenting fruit such as nectarine between 1.0 percent and 80 percent by volume. The attractant may also include artificial chemical additives to enhance attracting of the insects. The composition which is extracted by volatile solvents, does not include stearoptene. The oral toxin includes biological control agent selected from the group consisting of; *Bacillus thuringiensis, B. t. israelensis, B. sphaericus*, insect hormone mimics and insect growth regulators, and contact insecticides.

The extract may be adsorbed by fibrous materials to cause slow release of the extract into the environment. The extract may also be mixed into oily substance thereby causing a slow release of the extract into the environment.

According to the present invention there is provided a method for controlling insects, providing an insect bait including the mentioned insecticidal composition, including the steps of applying an effective amount of insect bait to a geographic area, providing a bait station, in the area and applying the insect bait onto bait station, by which insects are poisoned and trapped, applying may mean spraying insect bait on at least one substrate selected from the group consisting of vegetation trees, rocks and walls or smearing the bait on solid surfaces According to the present invention there is provided a method for controlling insects in a location, including the steps of determining location by sampling trees of an area, setting the location based on the number of floral and nectar trees in that location and spraying the composition mentioned above on nectar and trees, trapping the insects around nectar or trees using trap mechanism selected from the group consisting of: a suction mechanism creating an ingoing air stream, a adhesive which immobilizes the insects and electrical grid.

According to the present invention there is provided a method for controlling sugar feeding insects, which provides to said sugar feeding insects an insecticidal composition which includes a feeding stimulant including sugar and an attractant of the insects. The attractant is composed from an extract made from flowers and/or fruit and an oral toxin toxic to the insects. The oral toxin is selected from the group including: spinosad between 0.05 and 0.5 volume percent in solvent or phloxin B between 0.3 and 3 volume percent in solvent or Boric Acid between 0.1 and 3 volume % in solvent. The solvent may be either water or wine or other Hydrophilic fluids such as the alcohols ethanol, methanol and acetone. Producing an extract further includes mixing flowers of *T nilotica* in solvent and filtering.

BRIEF DESCRIPTION OF THE DRAWINGS

The invention is herein described, by way of example only, with reference to the accompanying drawings, wherein:

FIG. 1 is a schematic drawing of three main ingredients of the composition;

DETAILED DESCRIPTION OF THE PREFERRED EMBODIMENTS

Figure 2:
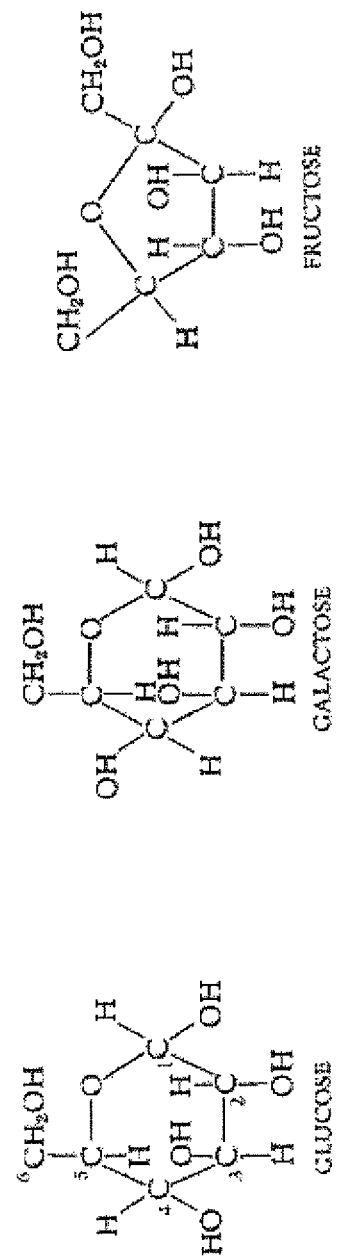
FIG. 2 (prior art) presents a chemical formula of the three common monosaccharides glucose and fructose for insect sugar diet.

The present invention is a method and device employing a novel composition for attracting and exterminating mosquitoes and other flies such as sand flies that feed and are attracted to sugars of plant origin. Specifically, the composition Includes feeding stimulants preferably sugar of plant origin, an attractant, and a toxin, for the attraction and extermination of the mosquitoes and other flies.

The principles and operation of a device employing a novel composition utilizes the sugar feeding behavior of blood-sucking flies, according to the present invention, may be better understood with reference to the experiments and the accompanying drawings.

Figure 1:
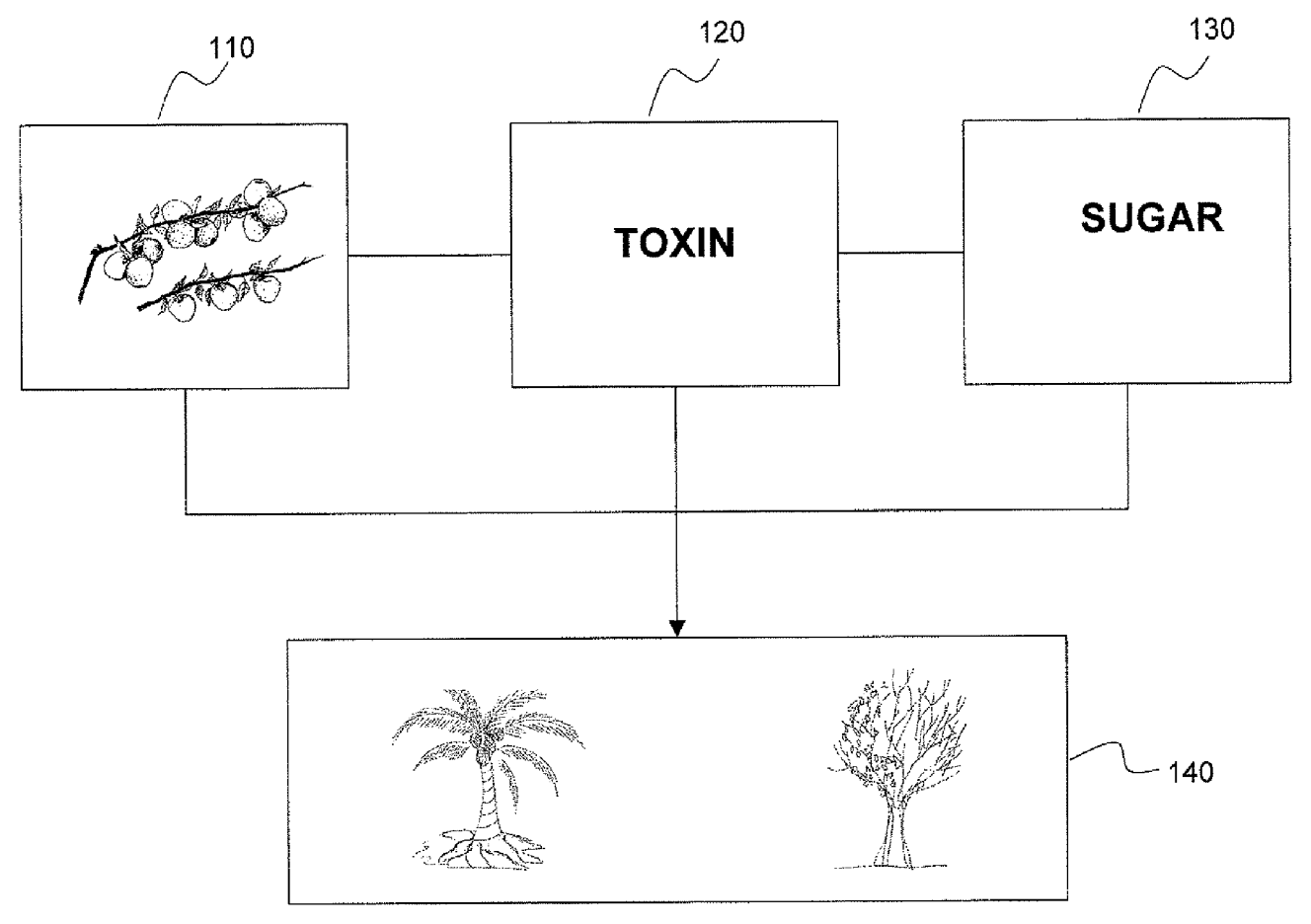

Before explaining embodiments of the invention in detail, it is to be understood that the invention is not limited in its application to the details of design and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting FIG. 1 exhibits Baits including fragrant floral or fruit attractant (110), sugary phagostimulant (130) and insect oral toxin (120) which are dispersed in suitable locations in target-insect habitat by spraying, or soaked in suitable fragrance slow release substrates Suitable carriers of the baits can be natural local environmental component (104) such as trees, thickets of vegetation and rock surfaces or artificially introduced elements such as porous plastic or cardboard plates Methods for Obtaining Attractants Attractants can be natural such as flowers either on the plant or collected and presented and it can be fruit in different stages of ripening or decay. Candidate flowers for extraction: *Acacia raddiana, Tamarix nilotica* and other *Tamarix* spp. and *Polygonum equisetiforme* and an example of fruit for extraction is over-ripe nectarine (*Prunus persica* var. *nectarina*). These can be extracted to isolate purify and store the components that attract sugar questing insects. A third possibility after the identification of the attractive components is to imitate them with the right combination of artificial chemicals and use the product as an insect attractant.

The methods for the extraction of fragrant substances include maceration, expression stream distillation in oily and organic solvents. Hydrophilic substances are concentrated in aqueous solutions. An "absolute", the extract obtained by extraction with volatile solvents or by enfleurage. It is the purest perfume material, retaining most of the plants aromatic constituents.

Enfleurage et maceration is a labor-intensive process that yields the highest quality of absolutes because it does not involve heat. Heat always alters the fragrance. It is used on delicate flowers that can not stand up to the high heat, and that continue to release essential oils after they have been picked. It works on the principle that fats absorb smells. Petals or other fragrant parts of a plant are steeped in fat or non-evaporating oil which will absorb their fragrance. This process is repeated several times with fresh flower heads until the oil is totally adsorbed with essential oil, the resultant. The fragrant substances are then retrieved from the fat by dissolving in an alcoholic solvent. The alcohol is then evaporated to leave the pure absolute.

Maceration is similar to enfleurage, a labor-intensive process. Maceration is used to extract essential oils from animal ingredients, vanilla and iris. These materials are steeped into vats of oil until the scented parts dissolve. The oil may be heated to speed up the process. Maceration takes long periods of time sometimes years.

Another method used for obtaining attractants is Expression, a simple technique where the extracted materials are cold pressed to extract their essential oils using rollers or sponges. There is no heat involved, leaving the oil to smell very close to the original plant.

Another method used for obtaining attractants is Distillation, a main method used for extracting essential oils. Distillation is based on the principal that when plant material is placed in boiling water, the essential oil in it will evaporate with the steam. Once the steam and oil have been condensed, the oil will separate from the water, and it can be collected. Plants are crushed to encourage them to release their oils. Plants are boiled in water, and the essential oils vaporize and rise up with the steam. The vapors are captured, and allowed to condense back into liquids. The essential oils are poured into Florentine flasks. Five to six tons of roses are needed to obtain one kilo of essential oil.

Extraction with volatile solvents without the removal of the stearoptene is preferably used for the purpose of obtaining attractants, according to the embodiment of the present invention. This method is used for delicate flowers whose odors are damaged by the high heat needed to boil water. The oils are extracted using solvents which have lower boiling points than water. Various substances such as ether or high-grade petroleum, which evaporate rapidly, are used in modern perfumery to dissolve essential oils from fragrant plant and animal materials. The usual method involves placing the fragrant material on perforated metal plates in a container (the extractor); the solvent is passed over them and led into a still, where it evaporates, leaving a semi-solid mass known as concrete, which contains the essential oil together with stearoptene. The oil can then be separated from the stearoptene by extraction with alcohol in a 'batteuse', producing the substance called absolute, which is the purest and most concentrated form of essential oil known.

Feeding Stimulants

Figure 3:
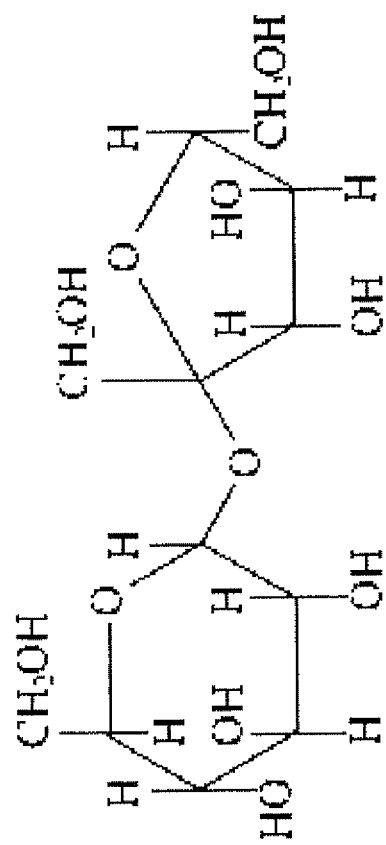
FIG. 3 (prior art) presents a chemical formula of a major feeding stimulant, sucrose.

The feeding stimulants are a sugar or a mixture of sugars. The term sugar refers to any monosaccharide, disaccharide, trisaccharides or oligosaccharide (containing 1, 2, 3, and 4 or more monosaccharide units respectively) that elicit insect feeding. Of the three common monosaccharides glucose and fructose are most important for insect sugar diet. (FIG. 2). A major feeding stimulant is sucrose (FIG. 3), a disaccharide of glucose (left) and fructose. Included in this list in addition to fructose, glucose, are also: galactose, maltose, lactose and mannose in any combination or chemical composition.

Toxins

Toxins include all the substances that kill insects and can be legally used for the purpose. Oral toxicants and insecticides have the priority since their effects are limited to insects that feed on the bait. Spinosad, boric acid and carbamate are an example for this type of toxicants. The list includes biological control agents such as *Bacillus thuringiensis*; *B. t. israelensis*; *B. sphaericus*; insect hormone mimics and insect growth regulators. It also includes contact insecticides of the different groups like permethrin or DDT.

Target Insects

Target insects are sugar feeding insects, mainly Diptera, particularly mosquitoes (Family Culicidae, genera *Anopheles, Culex* and *Aedes*) and sand flies (family Psychodidae). Of lesser importance are horse flies (family Tabanidae), non-blood sucking flies of the muscomorpha (*Cyclorrhapha*) group wasps and ants.

Methods of Applying the Bait

The attractant and sugar bait will be presented in different forms that suit the behavior of target insects and the conditions of the site. One basic way is to present both, the sugar bait plus toxin, and the attractant either with the other two substances or alone, soaked in suitable materials. The attractant is mixed in water with at least 10% sugar mixture and at least 0.001% spinosad.

The suffused materials can be placed at different points as specific larger bait stations or spread as grains over a wide area. A large variety of absorbing materials can be used as carriers of the sugar-insecticide-attractant combinations. To mention just a few: Cardboard, sheets of plastic foam and plates or grains of plaster of Paris. For example plaster of Paris plates 50×50 cm and 0.5 cm thick, or thick cardboards with the same surface size, suffused with sugar solution and toxin, accompanied by similar half a size plates suffused with floral attractant, can be hanged in at a height of ~1 m in a mosquito habitat with a distance of about 50 m between pairs of plates. Another version can be used in a sand fly habitat: Grains of plaster of Paris 2-5 mm in diameter, soaked with the three components of bait stations can be widely spread in a sand fly habitat with distances of 20-100 cm between grains.

The attractant may be mixed with a oily substance such as petroleum jelly which causes a slow release effect and the bait may be smeared on a solid surfaces of rock or wood, like the walls of a house and function in a dry state for an extended period.

Spraying: The chemical composition of the present invention can be sprayed on different type of vegetation on rocks and on walls. For example it is possible to spray trees near breeding sites of mosquitoes and the vegetation near breeding sites is a good target for spraying. In Mediterranean areas common plants at the margins of mosquito breeding sites are thickets of *Typha domingensis* and *Phragmites australis, Scirpus litoralis, Polygonum senegalense, Chenopodium murale, Conyza dioscridis, Epilobium hirsutus, Inula viscosa* and *Foeniculum vulgare*. Spraying will be particularly useful if the breeding site vegetation is thick and access to the water is difficult. The method of spraying depends on the size of the treated area. A hand sprayer may be sufficient for a private garden, spraying from the air would be necessary at the margins of large water bodies and there are several possibilities.

Spraying on a small area for experiments is with a 7 to 10 liter hand sprayer (for example Killaspray, Model 4005, Hozelock-ASL, Birmingham, England).

Hand sprayer: hand-held sprayers usually have an air pump which compresses air into the tanks and pressurizes the spray mixture. The pressure slowly drops as the liquid is sprayed. These sprayers operate at low pressures of 350 kPa (50 psi) or less and have small tanks of up to ten liters.

Similar back-pack sprayers: are fitted with a harness so the sprayer can be carried on the operator's back. Tank capacity may be as large as 20 liters.

Motorized sprayers: that typically produce more consistent sprayer outputs, and provide more uniform coverage than hand spraying have to be used in larger areas. Motorized sprayers typically produce more consistent sprayer outputs, cover the spray swath more uniformly, operate at constant speeds and result in much more uniform coverage than hand spraying. Motorized sprayers are also capable of higher pressure sprays where required to provide better coverage.

Motorized powered sprayers can provide high pressure sprays and power can be used to drive agitation systems, fans for air-assisted or air blast spraying, and transporting large volumes of spray mix. Properly equipped and operated, power sprayers can provide uniform coverage on a wide variety of targets. These systems can be mounted on tractors, trucks, trailers, and aircraft. Motorized sprayers may be used to supply spray mix to a hand gun or hand held boom with several nozzles. With this equipment, the spray uniformity will be similar to a hand operated sprayer. Provided with hand guns they are useful for spot treatments and treating small areas.

Boom Sprayers: Most sprayers distribute pesticides using a boom with spray nozzles spaced at regular intervals. Spraying the vegetation with the composition according to embodiments of the present invention can be done with low pressure boom sprayers that are suitable for spraying large plants with more foliage and may require finer droplets to obtain good coverage of the foliage. High pressure boom sprayers are often more suitable in these circumstances. High pressure sprayers require pumps, hoses, nozzles and other components that can develop and withstand the higher pressures.

Air-blast Sprayers: Most boom sprayers rely on pressure to move the spray mixture through a small opening in the nozzle and to create the small droplets and speed necessary to achieve good spray coverage of the target. In field crops good coverage is relatively easy to achieve where the target foliage is small and close to the nozzles. In tree fruits, especially with large trees, good coverage with conventional sprayers is more difficult to achieve. Air-blast sprayers direct the spray mixture from the nozzles into an air stream which transports the spray droplets to the target. Air-blast sprayers have a powered fan which forces air through an opening to generate high air speeds. Often the opening or manifold can be adjusted to ensure that the air stream is directed at the target.

In conventional air-blast sprayers most of the air movement is upward into the trees or target. Tower air manifolds are also available for air-blast sprayers which direct the air horizontally or even downwards towards the target. The horizontal or downwards air movement minimizes drift from air-blast sprayers.

Aerial applicators: On large surfaces of vegetation a belt of the bait preparation can be applied by either fixed-wing aircraft or by helicopters. The main advantage of aerial spraying is that it can be carried out quickly and at times when ground equipment cannot operate.

Constructions for Trapping

Bait station: a combined use of attractants for sugar questing insects and a mixture of sugary food bait (feeding stimulant) and insect toxin. The idea is that target insects follow the odor plume of the attractant, concentrate and feed on the sugar-toxin mixture of the bait and dye consequently. There are numerous variations for presenting such combinations in the field. All three components and the stations in which it is presented are spread at different distances according to the behavior of target insects and the structure (open or wooded areas) and properties (common wind directions) of the habitat.

Trap attractant combinations: attractants of plant origin are of all the types and preparations were previously described. Traps that are aimed at catching insects usually consist of a suction mechanism that creates an ingoing air stream. Insect engulfed by the air stream are propelled into a porous container, often made of net that allows the air flow to go through and keeps the insects inside. Different traps are provided with a source of light. UV or white that attracts insects to the traps. For blood feeding insects, released CO2 which can come from different sources is another common attractant and so are elevated temperature and humidity. Blood sucking is a trait of female mosquitoes, sand flies and other haematophagous Diptera and they require blood only at the beginning of gonotrophic cycles. Therefore a large part of the population at any given time is not responding to olfactory cues that lead to a host animal. The attractants of plant origin are a new family of attractants and they in will apparently have a more general effect on the target insect populations.

Thus, an embodiment of the present invention is to control sugar-feeding insects, especially adult insects in an area without resorting to ground and aerial spraying of chemical pesticides. Since the methods of the present invention are employed in a limited number of foci or specific small area, the environment is minimally affected, and the methods of the present invention adversely affect only a limited number of non-target organisms and there is no exposure of human population to pesticides. This is also the advantage compared to large scale programs of larval control in which the landscape is changed or larvicides are spread over large areas and indiscriminately affect the environment. A relatively small scale treatment is employed, which is required for having a significant effect by the present invention, consequently the amount of insecticide used, the required effort and the expenses are relatively low. Another advantage of the present invention is the enhanced attraction to sugar is common to all stages of adult mosquitoes whereas attractants to host animals affect only females that are searching for blood and not these that are developing eggs.

As such, those skilled in the art will appreciate that the conception upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described with respect to a limited number of embodiments, it will be appreciated that many variations, modifications and other applications of the invention may be made.

EXPERIMENTS

Experiment 1

Materials and Methods

The energy for the activities of female and male mosquitoes is provided by plant sugars or 'sugar meals' usually nectar from flowers and also from nectaries on leaves and stems, and honeydew excreted by homopterans. These are of particular interest in a situation of sugar shortage as the scarcity of flowers in arid areas. These plants are extreme attractants to nectar searching mosquitoes. Relying on this attraction we sprayed flowering *Acacia raddiana* trees in small mosquito infested oasis with sugar solution laced with oral insecticide Spinosad. Virtually the whole population of *Anopheles sergentii* was eliminated when lured by the fragrance of the flowers the mosquitoes fed on the poisonous sugar solution (Muller & Schlein, 2006). In the present study that was also carried out in the same sites, with no use of the attraction of local flowers but constructed and presented bait stations in which the attractant was fermenting ripe fruit.

The effect of attractive sugar baits including sucrose, juice of nectarine, blue food dye marker and oral insecticide, on *Anopheles sergentii* and *Aedes caspius* populations was studied in a small oasis in a southern desert of Israel. Whereas, feeding on similar baits without an insecticide was monitored as a control in a similar neighboring oasis. The insecticide caused a drastic decline in the number of mosquitoes. Compared to the control site the *An. sergentii* population was reduced to less than a tenth and that of *Ae. caspius* declined to a third. The majority of the mosquitoes, 76.0% of *An sergentii* females and 74.8% of *Ae. caspius* females, were marked by the food dye in the control site.

Study Sites

The study was carried out in two little oases that are enclaves of vegetation in a barren desert area, in the south of Israel where the annual rainfall is only 50 to 100 mm (Zohari, 1982). The oases were more than 5 km away from each other and from possible mosquito breeding sites. Both include small fresh water springs surrounded by dense vegetation that becomes thinner and altogether spreads on an area of about four to six hectares. Several *Acacia raddiana* (Mimosaceae) trees were scattered at different distances from the water. The experiments were carried out in the flowerless summer and autumn in October November 2006. The dominant riparian plant was *Phragmites australis* (Gramineae) and the desert plants included *Salsola cyclophylla, Suaeda fruticosa, Atriplex halimus*, Chenopodiaceae and *Alhagi graecorum* Papilionaceae (definitions as in Feinbrun-Dothan & Danin, 1991). *Anopheles sergentii* Theobald, an important malaria vector, (Service, 1993) *Aedes caspius* Pallas and *Culex* spp. were breeding in the springs but the larvae were almost inaccessible in the vegetation.

Bait

Bait solutions were prepared: These for the experimental site consisted of (A) ~85% juice of over-ripe to rotting nectarines (*Prunus persica* var. *nectarina*: Rosaceae), 5% wine, 10% W/V brown sugar ("Nature Sugar" brown, Louis Dreyfus, Israel), 0.5% W/V red food dye (Carmoisine E122, Stern, Natanya, Israel) and 0.04% WN oral insecticide of Spinosad ("Tracer"® Dow Agrosciences, Canada). In a similar solution (B) the portion of sugar was increased to 35%. W/V and the volume of fruit juice was adjusted accordingly. Both solutions were ripened for 48 hrs, in covered buckets, outdoors in the sun with daily temperature reaching ~300 C. Similarly prepared solutions without insecticide were used for the control site.

Disposable plastic bottles of 1.5 l soft drink with a hole of ~5 cm cut up at about ⅔ of the height were prepared. Cotton wick was inserted through the holes with both ends reaching down to the bottom of the bottles. The bottles were then inserted, bottom first into large, light colored, cotton flannel socks that had been thoroughly washed with water and dried. The socks were then wetted by dipping into solution B and about 0.5 liter of solution A was pored into each bottle. Thus fluid from inside the bottle was sucked through the wick when the external cover dried. The bottles were provided with a 60 cm umbrella shaped cover of plastic and 12 bottles with their covers were hung, dispersed, at a height of 1.5 to 2.0 m from branches of *A. raddiana* near the spring in the experimental and in the control site. The baits were presented on day six and they were changed after two weeks.

Monitoring

*An. sergentii* and *Ae. caspius* female populations in each site was monitored for 36 days with six miniature light traps (Model 512, John W. Hock, Gainesville, Fla.) placed in fixed positions, that were repeatedly hung overnight at a height of approximately 1 m.

Results

Figure 4:
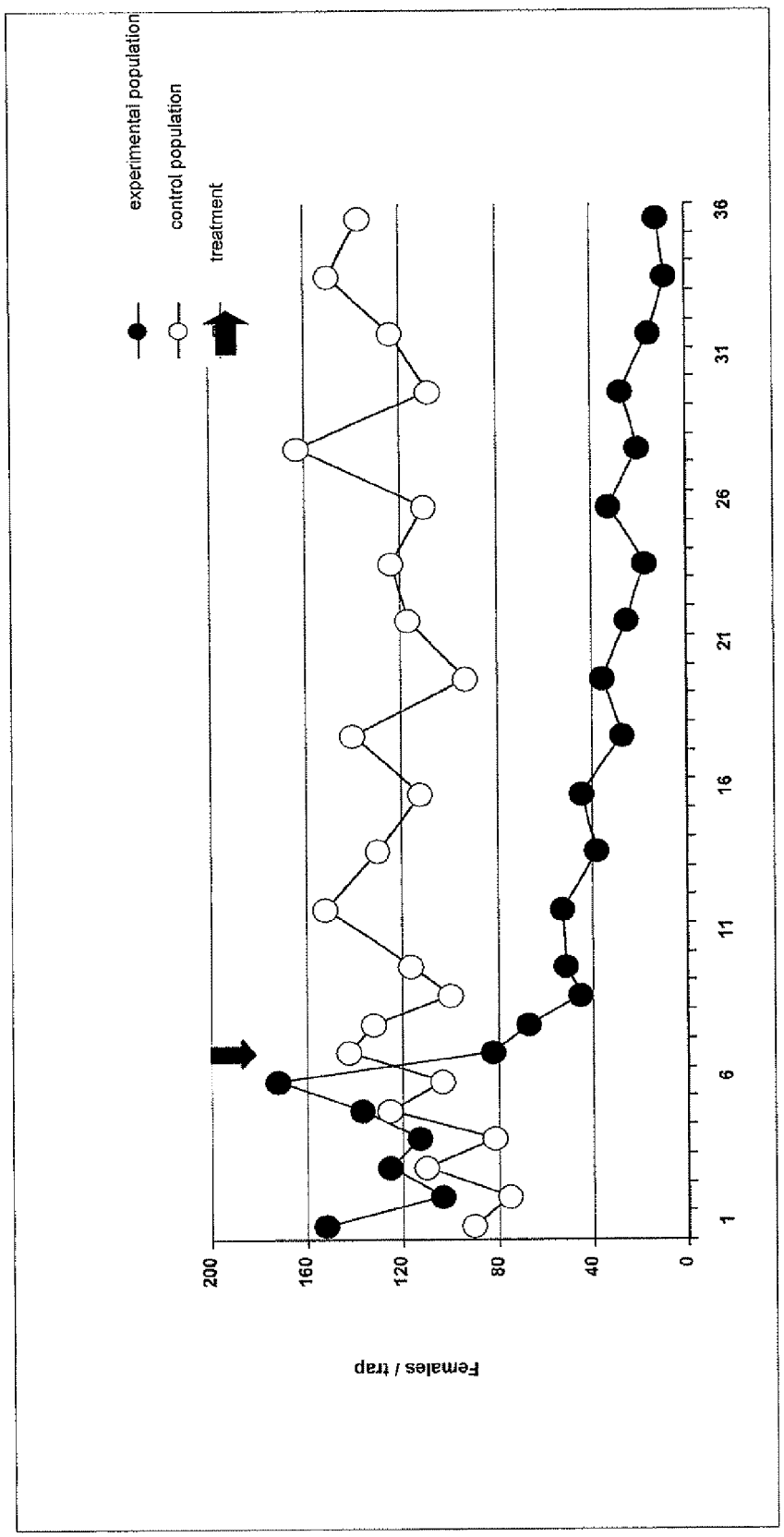
FIG. 4 is a graph showing the average catches of *Anopheles sergentii* females, according to the experiment of the present invention.
Figure 5:
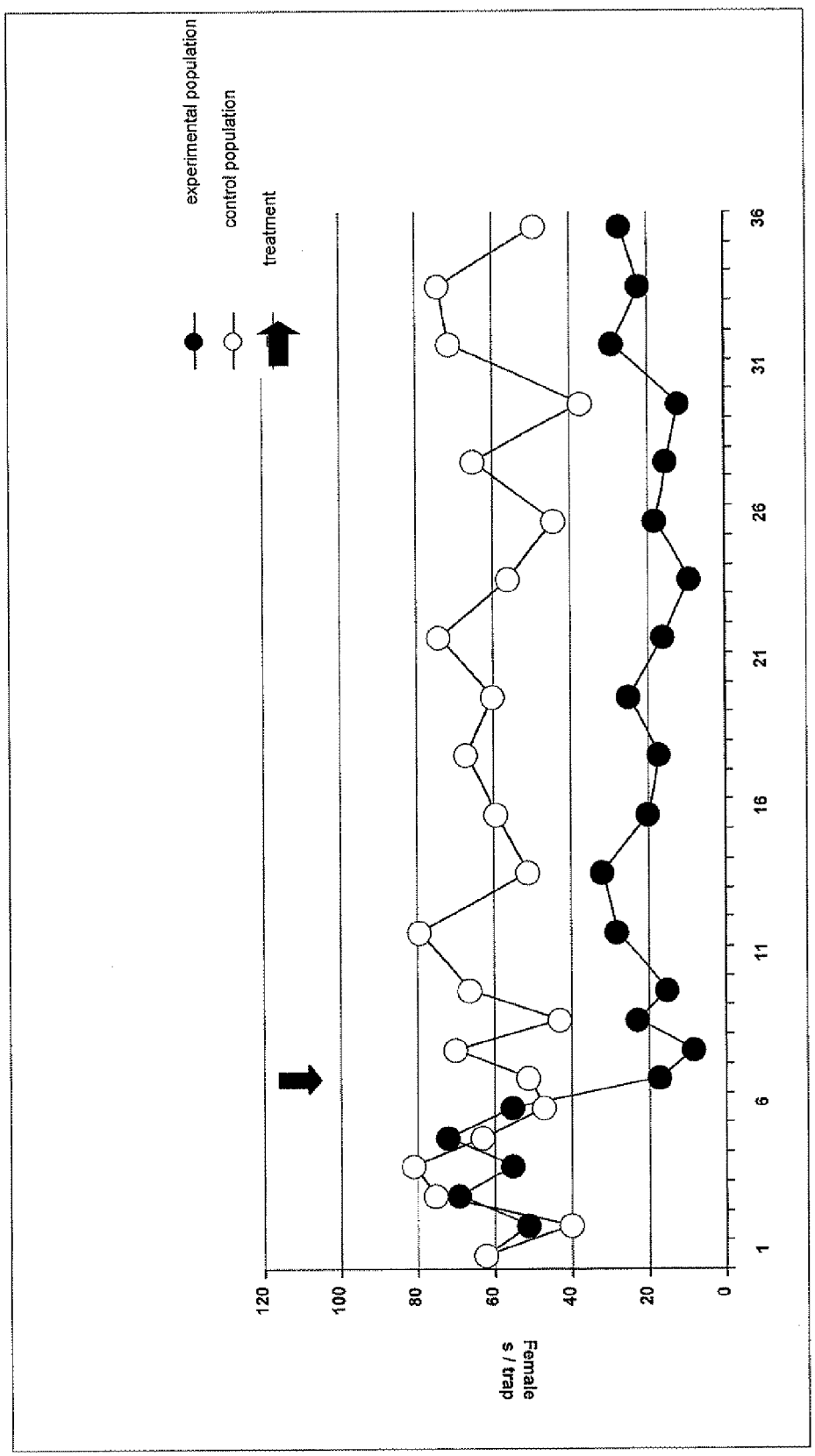
FIG. 5 is a graph showing the average catches of *Aedes caspius* females, according to the experiment of the present invention.

The catch of *An. sergentii* trapped in the experimental site was 133.6 females on average in the first six days. It declined to 82 females/trap immediately after presenting the baits and within 30 days gradually decreased to 11 females/trap. In the control site the average number of female mosquitoes/trap in the first six days was 97.3 and it increased to an average of 134.6 females/trap in the last 6 experimental days (FIG. 4). The effect on *Ae. caspius* was less pronounced. The average catch per trap in the first six days was 60.6 females. Afterwards with small fluctuations the average/trap in 30 days was 20 females. The catch of *Ae. caspius* in the control site amounted to 61.3 females/trap and and with fluctuations it was 60.35 females/trap for 30 days as (FIG. 5).

Dye Marking of Mosquitoes in the Control Site

The food dye label marked 52.8% of *An. sergentii* females in the first night and their proportion increased to 71.0% in night three. Afterwards their proportion fluctuated without a clear tendency between 68.1% and 93.3% and on average it was 76.0%. The labeling of *Ae. caspius* females was similar. From 39.2% labeled females in the first night it increased to 74.4% in the catch of night three, afterwards the lowest percentage of labeling was 68.6%, the highest was 92.5% and the average was 74.8%.

Discussion

In the present experiment the efficiency of attractive bait stations including oral insecticide for the control of mosquitoes was tested. Bait stations were similarly presented with the insecticide in an experimental oasis and without insecticide in a control site. Food dye marker was included in the baits in both cases, for labeling feeding mosquitoes as described by Schlein (1987). In the experimental oasis the insecticide caused a drastic decline in the number of mosquitoes. Compared to the control site the *An. sergentii* population was reduced to less than a tenth and that of *Ae. caspius* declined to a third. Feeding on similar baits without an insecticide in a control site, a similar neighboring oasis, marked on average 76.0% of *An sergentii* females and 74.8% of *Ae. caspius* females. It appears that the baits were similarly approached and fed upon by mosquitoes in the experimental and control oases since the rate of marking in the control site was similar to the decrease in mosquito populations in the experimental site. The high rate of dye marking and particularly the elimination of *An. sergentii* and *Ae. caspius* by the insecticide indicate that most of the mosquitoes obtained their sugar diet exclusively by feeding on the attractive baits. Both oases were 1 centered on springs that were mosquito breeding sites and there should have been a high multiplication rate. We therefore presume that most of the surviving mosquitoes in the experimental site and un-labeled mosquitoes in the control site were newly emerged mosquitoes.

The extensive mortality implied that bait stations that are central feeding sites may be used for efficient mosquito control. For this purpose it is plausible to use a solution of spinosad with sugar bait. Spinosad is basically an oral insecticide, it has very little toxicity to birds and mammals, it does not affect several insect groups and it was classified by the United States Environmental Protection Agency as an environmentally and toxicologically reduced risk material (Williams et al. 2003). Suitable places for this control approach might be in desert and savannah regions, particularly in sub-Saharan Africa, where the burden of malaria is increasing because of resistance to drugs, conventional insecticides and environmental changes (Greenwood & Mutabingwa 2002).

These areas include large scale irrigation projects, which increase the number of mosquitoes in arid and semi-arid areas. Such projects cover nearly half of the arable land in Africa (Ijumba & Lindsay 2001, Appawu et al., 2004) and there are similar projects in the desert in Pakistan ((Herrel et al., 2004).

Application of attractive bait: 10% of the vegetation around both ponds (experimental and control) of experiment 1 was sprayed with the mixtures described above. Application was in spots of 0.5-1 m2 on approximately every fifth thicket. Altogether about 10% of the vegetation in the experimental and control sites was treated. The experimental site received treatment with toxin and no toxin was used in the control. Mosquito populations were monitored for 35 days. Treatment was on the 6th day. Catches in the experimental site ranged between 65 to 90 female *Cx pipiens*/trap and afterwards it decreased to 3 to 18 females/trap. In the control site the catch was 40 females/trap during the whole period.

Experiment 2

Attraction of Flowers and Extracted Flowers of *Tamarix nilotica*

Open flowers of *T. nilotica* (weighing 9.5 kg) were put in 4000 ml hexane (Merck, reinst) in glass beakers and crushed. The fluid, 3700 ml hexane extract, was then filtered into bottles that were tightly closed. Aliquots of 80 ml extract were gradually soaked and dried in filter paper sheets (Din A 4, Blotting paper, Whatman Inc. NJ, USA) that were fan-shape folded with 1 cm ridges. Control similar papers were wetted with 80 ml untreated hexane. The experimental and control filter papers were attached to CDC like traps without light while other traps were provided with fresh *T. nilotica* flowering branches weighing ~1250-1500 gr. A line of traps (CDC-like miniature light traps (Model 512, John W. Hock, Gainesville, Fla.) provided with the above or other baits (five traps per bait, three repetitions) was presented overnight in mosquito habitats. In site 1 the average catch of control trap was 6.4 *Culex pipiens* mosquitoes. The catch of traps baited with extract was 9.8 times greater and that of flower baited traps was 78.1 times greater. In site 2 the average catch of control trap was 8.2 *Anopheles sergentii* mosquitoes. The catch of traps baited with extract was 5.6 times greater and that of flower baited traps was 5.5 times greater.

Experiment 3

The Use of Natural Floral Centers for Mosquito Control.

In traps baited with branches of common local plants, the highest, 60.5% of the total catch of *Culex pipiens*, was by flowers of *Tamarix jordanis* trees. The effect of the attraction was tested in the field. Experimental conditions: Selected control and experimental Mediterranean study sites were uncultivated areas stretching for about 500 m, along two channels, with *Tamarix jordanis* trees near their center. The mosquito population in the study sites was monitored for a month. On day six both sites were sprayed with sugar solution and additives using 7-liter hand sprayer (Killaspray, Model 4005, Hozelock-ASL, Birmingham, England). *T. jordanis* trees in the experimental site were sprayed with 7 to 15 liter solution of 20% weight/volume (w/v) sucrose, 2.0% w/v food blue No. 1 (Indigotine C.I. stern, Natanya, Israel) and 0.04% w/v oral insecticide Spinosad ("Tracer"®, Dow Agrosciences, Canada) in water. In the experimental site the spray of Spinosad caused a sudden decrease of 80%, from initial 255 mosquitoes/trap. The lowest level later was ~24 mosquitoes/trap while the yield in the control reached ~400 mosquitoes/trap. Re-growth of the population in the experimental site began 18 days after the spraying.

Experiment 4

Similar Use of Floral Attraction in the Desert.

Methodology as in the section above in experiment 3. The assumption that scarce flowering trees in arid areas are attractive, central sugar sources was tested in the southern desert of Israel. In traps baited with flowers of *Acacia raddiana, Tamarix nilotica* or *Ochradenus baccatus* the catch of *Anopheles sergentii* was ~35 to 75 times greater than with baits of flowerless branches. In a small isolated oasis, a spray of sugar and food-dye solution on the few flowering *A. raddiana* trees dye-labeled 80 to 90% of *An. sergentii*. In a similar oasis this spray with addition of oral insecticide virtually killed the local mosquitoe

What is claimed is:

1. A method for controlling insects, the method comprising the steps of:
   (a) providing an insect bait adapted to attract the insects, and to effect the insects to feed on said insect bait, mediated by an olfactory-cue-based attractant, wherein said insect bait lacks an active visual-cue element for a biting-fly sugar-source-foraging behavior-mode, said insect bait including:
      (i) a feeding stimulant, in a suitable amount to serve as an insect meal, said feeding stimulant including a sugar;
      (ii) an effective amount of an olfactory-cue-emitting attractant that is active for blood-sucking insects which are sugar-feeding, said effective amount exceeding an odor threshold associated with said blood-sucking insects, wherein said attractant includes a flower extract, a fruit extract, a sugar-rich plant-organ extract, or at least one component thereof; and
      (iii) a lethal concentration, in said insect meal, of an oral and/or contact toxin toxic to the insects; and
   (b) applying a sufficient amount of said insect bait to a designated geographic area, lacking an active visual-cue element for a biting-fly sugar-source-foraging behavior-mode, in order to control said blood-sucking insects.

2. The method according to claim 1, the method further comprising the steps of:
   (c) providing a bait station in said area; and
   (d) applying said insect bait onto said bait station;
   whereby the insects are poisoned and/or trapped within said bait station.

3. The method according to claim 1, wherein said applying includes spraying said insect bait on at least one substrate selected from the group consisting of: vegetation, trees, rocks, walls, and man-made substrates.

4. The method according to claim 1, wherein said applying includes smearing said bait on solid surfaces.

5. The method according to claim 1, wherein said applying includes presenting suitable substrates suffused with said bait.

6. A method for controlling insects in a designated location, the method comprising the steps of:
   (a) setting a location based on a number of nectar-containing blossoms of trees in said location, wherein said nectar-containing blossoms possess an effective amount of an olfactory-cue-emitting attractant that is active for blood-sucking insects which are sugar-feeding, wherein said location lacks an active visual-cue element for a biting-fly sugar-source-foraging behavior-mode, and wherein said effective amount exceeds an odor threshold associated with said blood-sucking insects; and (b) spraying on said trees an insect bait adapted to effect the insects to feed on said insect bait, mediated by said olfactory-cue-emitting attractant, wherein said insect bait lacks an active visual-cue element for a biting-fly sugar-source-foraging behavior-mode, said insect bait including:

(i) a feeding stimulant, in a suitable amount to serve as an insect meal, said feeding stimulant including a sugar; and (ii) a lethal concentration, in said insect meal, of an oral and/or contact toxin toxic to the insects.

7. The method according to claim 6, the method further comprising the step of:

(c) trapping the insects around said nectar or said trees using a trap mechanism, lacking an active visual-cue element for a biting-fly sugar-source-foraging behavior-mode, selected from the group consisting of: a suction mechanism creating an ingoing air stream, an adhesive that immobilizes the insects, and an electrical grid.

8. A method for controlling insects, the method comprising the step of:

(a) providing to the insects an insect bait adapted to attract the insects, and to effect the insects to feed on said insect bait, mediated by an olfactory-cue-based attractant, wherein said insect bait lacks an active visual-cue element for a biting-fly sugar-source-foraging behavior-mode, said insect bait including:

(i) a feeding stimulant, in a suitable amount to serve as an insect meal, said feeding stimulant including a sugar;

(ii) an effective amount of an olfactory-cue-emitting attractant that is active for blood-sucking insects which are sugar-feeding, said effective amount exceeding an odor threshold associated with said blood-sucking insects, wherein said attractant includes a flower extract, a fruit extract, a sugar-rich plant-organ extract, or at least one component thereof; and (iii) a lethal concentration, in said insect meal, of an oral and/or contact toxin toxic to the insects.

9. The method of claim 8, wherein said toxin is selected from the group consisting of:

spinosad between about 0.05 and 0.5 volume percent in solvent;

phloxin B between about 0.3 and 3 volume percent in solvent; and boric acid between about 0.1 and 3 volume percent in solvent.

10. The method of claim 8, the method further comprising the steps of:

(b) mixing flowers of Tamarix nilotica in a solvent; and (c) separating said flowers from said solvent in order to produce said extract.

11. The method according to claim 8, wherein at least one synthetic component of flowers, sugar-rich plant organs, and/or fruits is used in place of said flower extract, said fruit extract, or said sugar-rich plant-organ extract.

12. A bait station for controlling insects, the bait station comprising:

(a) a feeding stimulant, in a suitable amount to serve as an insect meal, said feeding stimulant including a sugar;

(b) an effective amount of an olfactory-cue-emitting attractant that is active for blood-sucking insects which are sugar-feeding, said effective amount exceeding an odor threshold associated with said blood-sucking insects, wherein said attractant includes a flower extract, a fruit extract, a sugar-rich plant-organ extract, or at least one component thereof;

(c) a lethal concentration, in said insect meal, of an oral and/or contact toxin toxic to the insects; and (d) at least one substrate for supporting said stimulant, said attractant, and said toxin;

wherein said stimulant, said attraction, said toxin, and said least one substrate lack and active visual-cue element for a biting-fly sugar-source-foraging behavior-mode; whereby the bait station is adapted to attract the insects, and to effect the insects to feed, mediated by an olfactory-cue-based attractant.

13. The bait station of claim 12, wherein said toxin is selected from the group consisting of:

spinosad between about 0.05 and 0.5 volume percent in solvent;

phloxin B between about 0.3 and 3 volume percent in said solvent; and boric acid between about 0.1 and 3 volume percent in said solvent.

14. The bait station of claim 13, wherein said solvent is an organic solvent.

15. The bait station of claim 12, wherein said stimulant includes said sugar at about 5% - 80% by weight.

16. The bait station of claim 12, wherein said attractant is selected from the group consisting of:

flower extract or at least one component thereof between about 0.01 percent and 0.5 percent by volume;

purified extract of fermenting fruit or at least one component thereof between about 0.01 percent and 0.5 percent by volume; and crude extract of fermenting fruit between about 1.0 percent and 80 percent by volume.

17. The bait station of claim 16, wherein said attractant includes an Ochradenus baccatus flower extract.

18. The bait station of claim 16, wherein said fermenting fruit includes nectarines.

19. The bait station of claim 12, wherein said attractant further includes artificial chemical additives to enhance attraction of the sugar-feeding insects.

20. The bait station of claim 12, wherein said attractant, as extracted by volatile solvents, does not include stearoptene.

21. The bait station of claim 12, wherein said toxin further includes a biological control agent selected from the group consisting of: *Bacillus thuringiensis, B.t. israelensis, B. sphaericus*, insect hormone mimics, insect growth regulators, and contact insecticides.

22. The bait station of claim 12, wherein said at least one substrate is a fibrous material for adsorbing and/or absorbing said attractant to cause slow release of said attractant into the environment.

23. The bait station of claim 12, wherein said attractant is mixed into an oily substance, thereby causing a slow release of said attractant into the environment.

24. The bait station of claim 12, wherein at least one synthetic component of flowers, sugar-rich plant organs, and/or fruits is used in place of said flower extract, said fruit extract, or said sugar-rich plant-organ extract.

* * * * *